United States Patent [19]

Gallagher

[11] 4,211,240
[45] Jul. 8, 1980

[54] INSPIRATORY FORCE ADAPTOR

[76] Inventor: Stephen F. Gallagher, 23 Eisenhower Dr., Norton, Mass. 02766

[21] Appl. No.: 949,864

[22] Filed: Oct. 10, 1978

[51] Int. Cl.² ............................................ A61B 19/00
[52] U.S. Cl. ...................................... 128/725; 128/276
[58] Field of Search ..................... 128/209, 210, 142.2, 128/145.6, 276, 351, 716, 717, 718, 720, 725, 726, 727, 728; 15/421, 330; 46/90; 272/99

[56] References Cited

U.S. PATENT DOCUMENTS 3,885,565  5/1975  Satchell ................................ 128/276

FOREIGN PATENT DOCUMENTS 880797  4/1943  France ..................................... 128/725

Primary Examiner—Henry J. Recla
Attorney, Agent, or Firm—Russell & Nields

[57] ABSTRACT

An inspiratory force adapter designed to be connected between a tracheostomy tube and an inspiratory pressure gauge, comprising a hollow plastic body adapted to be grasped by the thumb and finger of the operator and having a finger port adapted to be closed by another finger of the operator when the inspiratory force of a patient is to be measured. The plastic body is provided with finger positioning surfaces so located as substantially to eliminate undesirable twisting motions of the adapter under the forces exerted by the operator's fingers.

3 Claims, 3 Drawing Figures

INSPIRATORY FORCE ADAPTOR

BACKGROUND OF THE INVENTION

This invention relates to an improvement in the prior art type of inspiratory force adapter as shown in FIG. 1. Such an adapter consists of a molded plastic hollow body 10 having one tubular end 12 adapted to be connected onto the outer end of a tracheostomy tube 14, the other end of the tracheostomy tube being connected to the patient. The tubular member 12 extends to a ridge 16 which lies in a plane substantially perpendicular to the longitudinal axis of member 12. Beyond the ridge 16, body 10 has a tapered hollow section 18 which tapers down to a tubular output member 20 adapted to be connected to a flexible tube 22 which is connected to the usual inspiratory pressure gauge.

The upper face 24 of section 18 is disposed at an angle of about 45° with respect to the longitudinal axis of member 12 and is provided with a finger port 26 consisting of an opening into the hollow interior of body 10.

When in use, the tubular member 12 is grasped between the thumb 28 and second finger 30 of the operator. The sides of these two fingers rest against the ridge 16 which thus may be termed a "finger ridge". When it is desired to measure the inspiratory force exerted by the patient's diaphragm, the index finger 32 of the operator is pressed against the port 26 just before the patient begins the inhalation part of his breathing cycle. Thus, index finger 32 closes port 26 and the inhalation by the patient reduces the pressure within the system in which the adapter is located. Such reduction in pressure is measured by the pressure gauge connected to the tube 22 in accordance with the well known procedure for such a measurement.

A problem of such prior art device arises from the fact that any transverse motion imparted to the end of tracheostomy tube 14 is transmitted to the point at which the tracheostomy tube enters the incision in the patient's throat. Such motion is disturbing to the patient and otherwise highly undesirable. When in use, such prior art device tends to produce such motion to an undescriable degree.

The present invention recognizes that this is due to several factors. In each human hand, the thumb 28 is normally about an inch wide and is appreciably wider than the width of the second finger 30. Such difference is about two tenths of an inch. Therefore, when the thumb and index finger abut the finger ridge 16, the center 34 of the pressure area of the thumb 28 is displaced by a distance d, of about one-tenth of an inch from the center 36 of the pressure area of the second finger 30. This displacement of the points of maximum pressure by the thumb and second finger produces a couple which tends to rotate the body 10 around the point 34.

This invention also recognizes that the direction, along which the index finger 32 exerts its pressure lies along the line 38. Line 38 is substantially perpendicular to face 24 and passes through the center of finger port 26. The line, along which thumb 28 exerts its pressure through point 34, is designated as 40. It will be noted that line 38 intersects line 40 at a point substantially below point 34. As a result the forces exerted by the thumb 28 and the index finger create an additional couple tending to rotate the body 10 in the same direction as the couple between the thumb 28 and the second finger 30. Consequently, it is very difficult for the operator to restrain a tilting motion of body 10 during the operation of the device. As indicated above such motion is highly undesirable.

SUMMARY OF THE INVENTION

The present invention substantially eliminates the defects of the prior art by disposing the finger ridge at an angle other than a right angle with respect to the longitudinal axis of the adapter. The size of this angle is such that the portion of the finger ridge engaged by the operator's second finger is displaced, along the length of the adapter with respect to the position of the finger ridge engaged by the operator's thumb, by a distance of approximately one tenth of an inch. This arrangement brings the center of the operator's thumb into a direct line with the center of the operator's second finger in a direction transverse to the adapter. This eliminates one of the twisting couples described above. In addition the location of the face of the adapter, having the finger port, is located so close to the finger ridge that the line perpendicular to said face and passing through the center of the finger port, intersects the center line of the operators thumb at substantially the center of the surface of the adapter as engaged by said thumb. This eliminates the second twisting couple described above.

DETAILED DESCRIPTION OF THE PREFERRED EMBODIMENT

Figure 1:
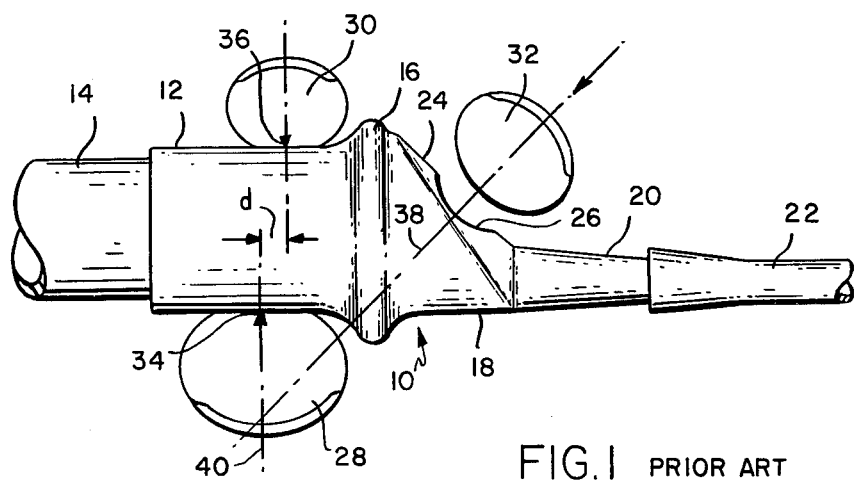
FIG. 1 is a side view of the prior art adapter of which the present invention is an improvement.
Figure 3:
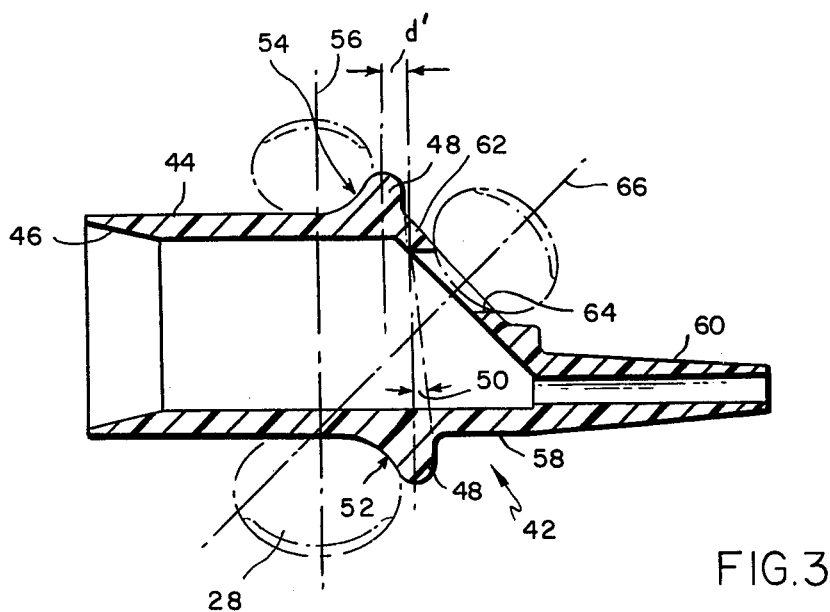
FIG. 3 is a cross section taken along line 3—3 of FIG. 2.
Figure 2:
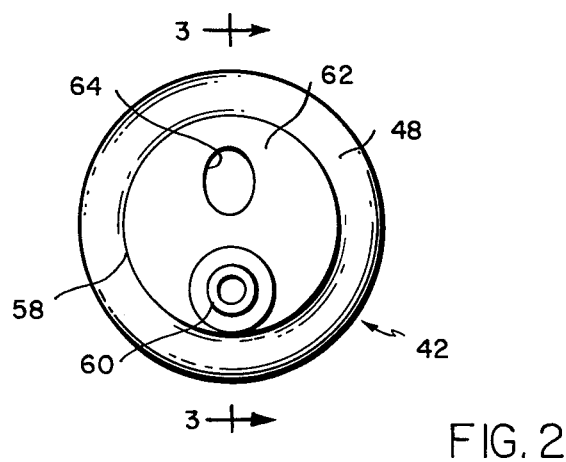
FIG. 2 is an end view of a preferred embodiment of the present invention.

In the drawings 42 is a hollow plastic moulded body comprising the adapter of this invention. The adapter 42 is formed with a tubular member 44 having a tapered end in its outer ends adapted to receive and retain the end of a standard tracheostomy tube. Tubular member 44 extends to a finger ridge 48 disposed in a direction along an acute angle 50 with respect to a diameter of the member 44. The lower portion of ridge 48 has a thumb engaging surface 52, while the upper portion of edge 48 has a second finger engaging surface 54. The upper portion of ridge 48 is displaced toward the outer end of tubular member 44 with respect to the lower portion of edge 48 by distance d' approximately one tenth of an inch so that the centers of surface 52 and 54 are likewise displaced by approximately one tenth of an inch. It has been determined that a displacement of this size will cause the thumb 28 and second finger 30 of virtually any operator to have their centers aligned along a line 56 of perpendicular to the longitudinal axis of member 44. This construction substantially eliminates the first of the undesirable couples described above.

Beyond the ridge 48, member 42 has a tapered hollow section 58; which tapers down to a tubular output member 60. The upper face 62 of section 58 is disposed at an angle of almost 45° with respect to the longitudinal axis of member 42 and is provided with a finger port 64. In this improvement, the displacement of the upper face 62 to be moved closer to the position occupied by operator's thumb 28 in engagement with ridge surface 52. In addition, other parameters of the member 42 are adjusted so that a line 66 extending through the center of finger port 44 and perpendicular to face 62 intersects the lower surface of member 44 at substantially the position occupied by the center of the operator's thumb 28 in engagement with surface 52 which is about one half inch from surface 52. This is the line along which the force of operator's index finger 32 closed upon the finger port 64 is exerted on the body 42. This construction substantially eliminates the second of the undesirable couples described above.

An inspiratory force adapter constructed in accordance with the principles described above is found to be remarkably free of the deleterious movements encountered in the operation of the prior art device.

It is to be understood that various modification may be made in the preferred embodiment as described above. For example, instead of providing a thumb engaging surface and a second finger engaging surface by a continuous ridge extending all around the adapter, separate projections at the top and bottom of the adapter may be provided for such purpose. Various other modifications will suffest themselves to those skilled in the art.

What is claimed is:

1. An inspiratory force adapter comprising:
    (a) an elongated hollow tubular body member having first and second ends and an air passage extending therethrough adapted to be grasped between the thumb and a finger of an operator;
    (b) said tubular body being provided with a finger port adapted to be closed by an index finger of said operator; said finger port constituting an opening from said air passage to the outside atmosphere;
    (c) the exterior of said tubular body member being provided with opposing finger positioning surfaces, the first of said surfaces being a thumb locating surface adapted to be engaged by the side of the thumb of said operator and the second of said surfaces being a finger locating surface adapted to be engaged by the side of said first named finger; the perpendicular central axes of said surfaces being aligned, with respect to each other and being transverse to the longitudinal axis of said body member, a ridge encircling said body member and abutting said surfaces, said surfaces being located along the peripheral surface of said body member between said first end and said ridge, said ridge being disposed with its transverse plane being oriented at an angle with respect to said perpendicular central axes of said surfaces, such that the difference between the distance from the ridge to said central axis of the thumb locating surface and the distance from the ridge to said central axis of said finger locating surface is substantially one tenth of an inch, said finger port being located on said tubular body member between said ridge and said second end and opposite said thumb locating surface.

2. An adapter as in claim 1 in which said finger port is formed in a wall of said tubular member disposed at an angle with respect to the transverse plane of said tubular member; such angle being of a magnitude so that a line perpendicular to said wall and passing through the central area of said port, intersects a wall of said tubular member at a distance from said thumb locating surface of substantially one half inch.

3. An adapter as in claim 2 in which said angle of said wall is substantially forty-five degrees.

* * * * *